United States Patent [19]
Lavyne

[11] Patent Number: 5,123,403
[45] Date of Patent: Jun. 23, 1992

[54] SUCTION NERVE ROOT RETRACTOR

[76] Inventor: Michael H. Lavyne, 11 Greenridge Dr., Chappaqua, N.Y. 10514

[21] Appl. No.: 728,152

[22] Filed: Jul. 10, 1991

[51] Int. Cl.⁵ .............................................. A61M 1/00
[52] U.S. Cl. ..................................... 128/20; 604/902; 606/1
[58] Field of Search ..................... 128/20; 604/93, 118, 604/119, 128, 313, 314, 902; 606/1; 433/91-96, 184

[56] References Cited

U.S. PATENT DOCUMENTS

| | | | |
|---|---|---|---|
| Re. 24,693 | 9/1959 | Thompson | 433/93 |
| D. 248,870 | 8/1978 | Hass . | |
| 674,650 | 5/1901 | Lundborg . | |
| 1,042,133 | 10/1912 | Marshall . | |
| 1,930,712 | 10/1933 | Girvin | 433/96 |
| 2,255,657 | 9/1941 | Freedman | 433/91 |
| 2,507,938 | 5/1950 | Smith | 433/94 |
| 3,029,513 | 4/1962 | Fletcher | 433/94 |
| 3,333,340 | 8/1967 | Boisvert | 433/91 |
| 4,049,000 | 9/1977 | Williams | 128/20 |
| 4,676,780 | 6/1987 | Lee . | |
| 4,772,260 | 9/1988 | Heyden . | |
| 4,883,426 | 11/1989 | Ferrer | 433/91 |

OTHER PUBLICATIONS

A Variable-angled Suction Nerve Root Retractor for Lumbar Spine Surgery, *Neurosurgery*, vol. 29, No. 3, 1991.

*Primary Examiner*—Stephen C. Pellegrino
*Assistant Examiner*—Glenn K. Dawson
*Attorney, Agent, or Firm*—Brumbaugh, Graves, Donohue & Raymond

[57] ABSTRACT

There is disclosed according to the invention a suction retractor for retraction of a nerve root during surgery, comprising a suction tube having an interior and exterior diameter, and a suction end and a base end, a retractor member having a tubular portion slidably positioned over the suction tube, said tubular portion having an interior diameter slightly larger than the exterior diameter of the suction tube such that the tubular portion is axially and rotatably slidable on the suction tube by manual pressure and yet sufficiently tight that it frictionally engages the suction tube and does not move except by said manual pressure, the retractor member having a spatula portion extending from said tubular portion axially toward and radially away from the suction end of the suction tube, the spatula portion adapted to permit the retraction of a nerve root during surgery.

11 Claims, 1 Drawing Sheet

SUCTION NERVE ROOT RETRACTOR

BACKGROUND OF THE INVENTION

The present invention relates to a suction retractor for use during surgery, particularly lumbar spinal disc surgery.

During lumbar spinal surgery, the surgeon typically uses a suction tube (e.g. a #8 Frazier disposable sucker) in the open incision. In order to extract disc fragments from the spine, the nerve root usually must be retracted. Because it is often difficult for a surgical assistant to have a sufficient view of the wound, the surgeon will perform the retraction and extraction without assistance by using the suction tube in one hand to gently retract the nerve root, and use a pituitary rongeur in the other hand to extract the disc fragments.

While this procedure works satisfactorily in the vast majority of cases, it can happen that because the suction tip is round, the nerve root will slip over the suction tip. If this happens, the nerve root may catch in the suction tip, thereby inadvertently traumatizing the nerve root. To some extent, the William's suction retractor (Codman, Randolph, Mass.) with a fixed blade a few millimeters from the suction tip has been helpful in preventing this complication. However, the fixed blade forces the surgeon to accommodate to the fixed angle of retraction, rather than the other way around.

BRIEF DESCRIPTION OF THE INVENTION

There is disclosed according to the invention a suction retractor which has, in addition to the suction tube, a retractor portion slidable over the suction tube. The retractor has a tube portion which frictionally engages the suction tube, and a spatula-like end portion which curves away from the suction end of the suction tube. The retractor portion can be positioned both axially and rotatably on the suction tube to suit the needs and preferences of the surgeon in the circumstances. Once properly positioned, i.e. merely by pushing it with one's finger, it retains sufficient frictional engagement with the suction tube so as to permit retraction of the nerve root without substantial further movement. If position adjustment is required, this can be accomplished by gentle pressure, either with the hand or against a non-sensitive surface of the wound.

DESCRIPTION OF THE PREFERRED EMBODIMENT

Figure 1:
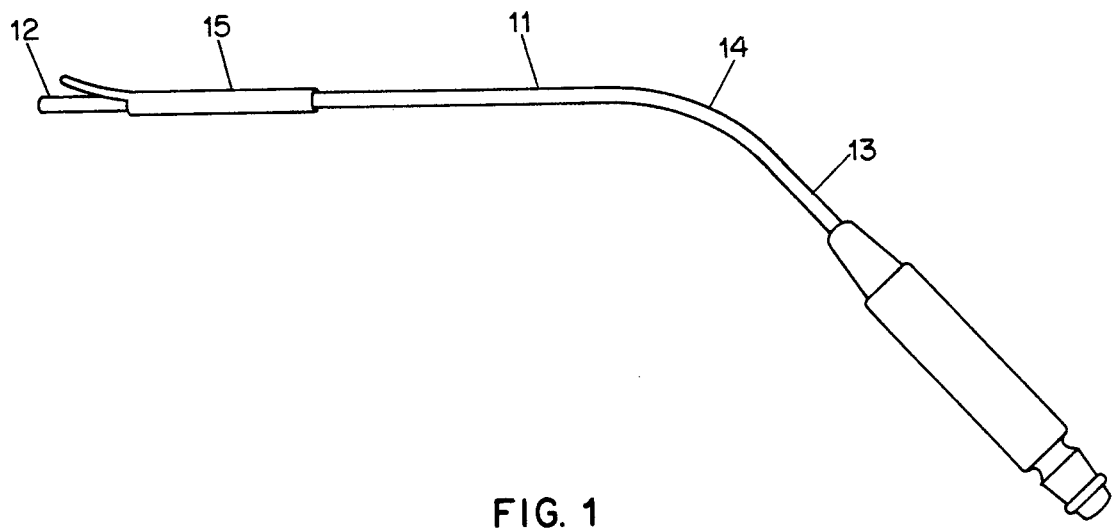
FIG. 1 is a side view of a suction retractor according to the invention.

Looking to FIG. 1, the suction retractor according to the invention has a suction tube 11 with a suction end 12 and a base end 13. In the preferred embodiment, the suction tube has a bend 14 (e.g. between 25°–50°, preferably about 40°) between the ends.

Figure 2:
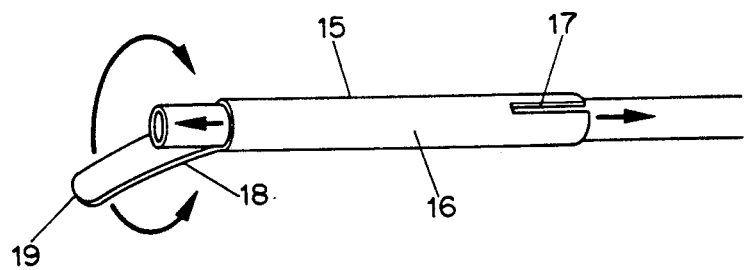
FIG. 2 is a perspective view of the tip portion of the retractor of FIG. 1.

As shown in FIG. 2, there is provided a retractor member 15 slidable over the suction tube. The retractor member has a tubular portion 16, the interior diameter of which is sized such that it is only slightly larger than the exterior diameter of the suction tube. So configured, the tubular portion 16 may rotate about the axis of the suction tube (as shown by the curved arrows) or move axially along the suction tube, as shown by the straight arrows. The relative sizing of the suction tube 11 and retractor tubular portion 16 are such, however, that the tubular portion frictionally engages the suction tube with sufficient force to retain its set position during surgery.

In order to facilitate the setting or adjustment of the desired frictional force, a slot 17 may be provided. By crimping or opening this slot, the frictional engagement may be increased or lessened as desired.

It has been found that cut lengths of #9 Frazier metal suckers will fit over a #8 Frazier sucker with the proper frictional engagement. Cut lengths approximately three cm in length are typical.

In order to form a spatula portion on the end of the retractor member, at least half, and preferably about two thirds, of the circumference of the tube is cut away along one end of the tubular member. Typically about a one centimeter length is cut away. The remaining portion along the cut length (typically comprising one half to one third the tube circumference) is flattened and honed into a slightly curved spatula-like tip retractor 18 (e.g. similar in configuration to a Penfield #4).

As can be seen in the drawings, the spatula portion extends from the tubular portion axially toward and radially away from the suction end 12 of the suction tube 11.

The tip edge 19 of the retractor may be curved to avoid tissue damage during the retraction procedure.

While the suction retractor according to the invention is primarily intended for use as a nerve root retractor for use during spinal surgery, it will be appreciated that it may find use during any type of surgery wherein a suction retractor is necessary or desirable.

I claim:

1. A suction retractor adapted for retraction of a nerve root during surgery, comprising
    a suction tube having an interior and exterior diameter, and a suction end and a base end,
    a retractor member having a tubular portion slidably positioned over said suction tube, said tubular portion having a base end toward the base end of the suction tube and a remote end remote from the base end of the suction tube, and having an interior diameter slightly larger than the exterior diameter of the suction tube such that said tubular portion is axially and rotatably slidable on said suction tube by manual pressure and yet sufficiently tight that it frictionally engages said suction tube and does not move except by said manual pressure,
    said retractor member having a spatula portion extending from the remote end of said tubular portion axially away from the base end of the tubular portion and radially away from the suction end of the suction tube,
    said spatula portion adapted to permit the retraction of a nerve root during surgery.

2. A suction retractor according to claim 1, wherein said retractor member is comprised of a unitary metal tube with at least half of the metal tube's circumference cut away along a portion of the metal tube's length at an end of the metal tube toward the suction end of the suction tube, and wherein the remaining metal tube's circumference along said portion of said metal tube's length is at least partially flattened and shaped to form said spatula portion.

3. A suction retractor according to claim 2, wherein said spatula portion is curved radially away from the suction tube.

4. A suction retractor according to claim 2, wherein the spatula portion is approximately one centimeter long.

5. A suction retractor according to claim 2, wherein said retractor member includes a slot cut into said tubular portion, said slot adapted to be crimped or opened so as to adjust the force with which the tubular portion frictionally engages the suction tube.

6. A suction retractor according to claim 1, wherein said spatula portion is curved radially away from the suction tube.

7. A suction retractor according t claim 1, wherein the spatula portion is approximately one centimeter long.

8. A suction retractor according to claim 1, wherein the suction tube is substantially straight at the suction end, and has a bend between the suction end and the base end.

9. A suction retractor according to claim 8, wherein the angle of said bend is between about 25° and 50° relative to a longitudinal axis of the base end of the suction tube.

10. A suction retractor according to claim 8, wherein the angle of said bend is about 40°.

11. A suction retractor according to claim 1, wherein said retractor member includes a slot cut into said tubular portion, said slot adapted to be crimped or opened so as to adjust the force with which the tubular portion frictionally engages the suction tube.

* * * * *